United States Patent [19]

Franz et al.

[11] Patent Number: 4,801,739

[45] Date of Patent: Jan. 31, 1989

[54] OLIGOMERIC HYDROXYCARBOXYLIC ACID DERIVATIVES, THEIR PRODUCTION AND USE

[75] Inventors: Joachim Franz, Riehen; Walter Prikoszovich, Allschwil; Zdenek Brich, Binningen, all of Switzerland

[73] Assignee: Sandoz Ltd., Basel, Switzerland

[21] Appl. No.: 562,470

[22] Filed: Dec. 16, 1983

[30] Foreign Application Priority Data

Dec. 17, 1982 [CH] Switzerland ................................ 7372
Dec. 17, 1982 [CH] Switzerland ................................ 7373

[51] Int. Cl.$^4$ ............................................. G07C 69/66
[52] U.S. Cl. .................................................... 560/185
[58] Field of Search ................ 560/179, 185; 562/450; 260/397.2

[56] References Cited

U.S. PATENT DOCUMENTS

| | | | |
|---|---|---|---|
| 2,362,511 | 11/1944 | Teeters | 528/361 |
| 3,141,030 | 7/1964 | Buddemeyer et al. | 560/179 |
| 3,440,241 | 4/1969 | Siddall | 260/397.2 |
| 3,773,919 | 11/1973 | Boswell et al. | 424/78 |
| 4,011,312 | 3/1977 | Reuter et al. | 424/78 |

FOREIGN PATENT DOCUMENTS

| | | |
|---|---|---|
| 0026599 | 4/1981 | European Pat. Off. . |
| 52510 | 5/1982 | European Pat. Off. . |
| 58481 | 8/1982 | European Pat. Off. . |
| 936746 | 12/1955 | Fed. Rep. of Germany ...... 560/179 |

OTHER PUBLICATIONS

Barber et al, *Laboratory Practice*, Apr. 1964, pp. 322–326.

Ojima et al, *Chemistry Letters*, 81, No. 6, Jun. 1981, pp. 823–826.

*Primary Examiner*—Donald B. Moyer
*Assistant Examiner*—Bruce D. Gray
*Attorney, Agent, or Firm*—Gerald D. Sharkin; Robert S. Honor; Walter F. Jewell

[57] ABSTRACT

A product of an oligomer derived from glycolic acid and/or lactic acid, the oligomer having a molecular weight of from 500 to 10,000, the free carboxylic acid group of the oligomer being at least partially in the form of an amide with an amino acid or an ester with a sterol may be used as a matrix material for depot forms, containing pharmacologically active agents.

5 Claims, No Drawings

OLIGOMERIC HYDROXYCARBOXYLIC ACID DERIVATIVES, THEIR PRODUCTION AND USE

The invention relates to oligomeric hydroxycarboxylic acid derivatives, in particular of lactic acid and/or glycolic acid, their production and use, e.g. in the production of depot forms of pharmacologically active agents, including salmon calcitonin and bromocriptine.

There have been various proposals in the art to produce depot forms of pharmacologically active agents, e.g. polypeptides, in the form of a matrix of a polymer, including oligomers, of glycolic acid and/or lactic acid which has the pharmacologically active agent dispersed throughout. The depot form may be administered orally, e.g. in the form of a suspension or preferably sub-cutaneously or intramuscularly e.g. in the form of a suspension, or sub-dermally as an implantation, e.g. in the form of rods, spheres, discs, films or pellets. The matrix comes into contact with body fluids and releases the active agent over a prolonged period of time thereby providing sustained action of the active agent. The polymer itself slowly degrades into non-toxic products.

The general principles are disclosed in U.S. Pat. No. 3,773,919 (DuPont) and in the following Patent Publications.

The European patent publication No. 26,599 (Lilly) discloses copolymers, including oligomers, of lactic acid and glycolic acid having molecular weights of 6,000 to 35,000, preferably of 15,000 to 30,000. Depot forms produced from such polymers are disclosed for use in humans. The preferred use is, however, for depot forms to be administered to animals raised for their meat or other food products to be consumed by humans.

The European patent application No. 52510 (Syntex) discloses microcapsule injectable depot forms of polypeptides in polymers of lactic acid, and copolymers of lactic acid and glycolic acid, having molecular weights of 20,000 to 100,000.

The European patent publication No. 58481 (ICI) discloses depot forms of polypeptides in polymers of lactic acid and copolymers of lactic acid and glycolic acid having molecular weights ranging from somewhat lower than 15,000 up to 240,000. A large number of suitable classes of polypeptides are listed including the calcitonin class. There is no further disclosure of any specific calcitonin and no specific example of a calcitonin depot form.

The matrix polymers of high molecular weight may have the disadvantage of a considerable long degradation time in the body fluids compared to the active agent release time, with the result that when the active agent has been completely released from the polymer matrix, an additional dosage can not be safely administered immediately afterwards, since this may lead to an undesired and dangerous accumulation of polymer matrix material.

U.S. Pat. No. 4,011,312 (American Home) discloses the use of co-oligomers of lactic acid and glycolic acid produced according to U.S. Pat. No. 2,362,511 (Du-Pont) to form a pharmaceutical depot form containing an anti-biotic for the treatment of mastitis in cows, e.g. by infusion of a suspension or placement of a bougie into the udder. The oligomers are stated to have a molecular weight of about 1,000 to 2,000, and a lactic acid content of from 20 to 40 mole percent.

The use of simple derivatives of polymers of lactic acid and/or glycolic acid in pharmaceutical depot forms has not been reported although U.S. Pat. No. 2,362,511 mentioned above does disclose the reaction of glycolic acid with amino acids leading to co-polymers, useful in non-medical areas.

The present invention sets out to overcome the above disadvantages, and to provide a useful pharmaceutical depot form for clinical use.

Furthermore the depot forms made from the oligomers according to the invention may have the advantage of a drug release time which is still satisfactorily long e.g. several weeks and suitable to incorporate a wide variety of, e.g. water-soluble active agents.

Additionally the polymers according to the invention may be easily handled, e.g. less sticky than e.g. the corresponding free acid polymers, and thus be easily administered as microcapsules through an injection needle.

The present invention provides in one aspect a modified oligomer comprising units of lactic acid and/or glycolic acid the oligomer moiety having a molecular weight of from 500 to 10,000, in which the terminal carboxy group is in the form of an amide of an amino acid or an ester of a sterol.

In another aspect the invention provides a mixture comprising the modified oligomer in admixture with unmodified oligomer The lactic acid units may be in optically pure form (D- or L-lactic acid) or mixtures of thereof, e.g. racemic form (D,L-lactic acid). The oligomer may contain other units, particularly other hydroxycarboxylic units, if desired.

Preferably the oligomer has a molecular weight of 500 to 5,000, especially 750 to 5,000. Examples of molecular weights are 500 to 1,000 for oligomers based mainly on lactic acid and about 1,000 to 3,000 based mainly on glycolic acid, determined by acid number and/or lowering of vapour pressure.

The oligomer contains preferably at least 40%, especially 70%, more especially 70 to 80%, by weight of lactic acid units. Preferably the molecular weights of such oligomers are from 750 to 5,000, especially 750 to 3,000, particularly 750 to 2,000.

As regards glycolic acid units conveniently the oligomer contains up to 60% by weight, preferably 10 to 50%, especially 20 to 30% of glycolic acid units. The oligomers containing up to 60% of glycolic acid units preferably have a molecular weight of 1,000 to 5,000, especially 1,000 to 3,000, particularly 1,000 to 2,500.

Other oligomers are for example those containing at least 70% by weight of glycolic acid units. These oligomers preferably have a molecular weight of 750 to 1,500.

When the oligomer contains hydroxycarboxylic acid units other than those of glycolic acid or lactic acid, these preferably are of e.g. -hydroxycaproic acid. Preferably such units comprise a maximum of 30% by weight of the oligomer moiety. Preferably less than 5% or no such units other than lactic acid or glycolic acid are present.

Suitable sterols are physiologically acceptable and non-toxic sterols. Preferably the sterols are naturally occurring. Especially preferred sterols include cholesterol and dihydrocholesterol.

Suitably the amino acids are physiologically acceptable and non-toxic amino acids. Preferably these are naturally occurring. If desired the amino acid may be in the form of a peptide. Neutral, acidic or basic amino acid may be employed. Suitable neutral amino acids are those from glycine, alanine, valine, leucine, phenylalanine, proline or tryptophan. Suitable acidic amino acids are glutaminic or aspartic acid and basic amino acids include arginine, lysine, histidine or ornithine.

Preference is given to aromatic amino acids, such as phenylalanine and tyrosine or their peptides.

In another aspect the present invention provides a process for the production of the products according to the invention which comprises appropriately amidating or esterifying an oligomer comprising units of lactic acid and/or glycolic acid, the oligomer having a molecular weight of from 500 to 10,000.

The products of the invention and esters may be produced in conventional manner using e.g. known condensation processes to produce amides and esters. Preferably at least an equimolar quantity of amino acid or sterol is present. Preferably dehydration conditions, e.g. heating to distil off water, are employed.

The reaction mixture is preferably heated to from about 150° to about 200° C. Water may conveniently be distilled off.

Preferably no catalyst is used which might polymerise the oligomeric hydroxycarboxylic acids and thus increase their molecular weights. Activation of reacting groups may be desirable. For example in an amidation reaction with an amino acid, the carboxyl group of the free oligomeric hydroxycarboxylic acid is preferably activated in known manner, e.g. by imide formation.

The products according to the invention may include mixtures of the esterified or amidated oligomeric hydroxycarboxylic acids, the free oligomeric hydroxycarboxylic acids and the sterols or amino acids. However, the reaction may be carried out in such a way that essentially pure esterified or amidated oligomeric hydroxycarboxylic acids are produced.

The quantity of free oligomeric hydroxycarboxylic acids still present may be expressed on the basis of the acid number of the product and may be determined in conventional manner, most conveniently by titration of the product against a KOH solution. The products according to the invention preferably have an acid number of up to 20, for example between 10 and 20.

In addition, the products may be purified in conventional manner for analogous compounds. The amount of free oligomeric hydroxycarboxylic acids and of sterols or amino acids is thereby reduced. Column chromatography e.g. with silicagel is the preferred method. In this way, products according to the invention may be obtained which have an acid number of below 2, preferably below 1.5.

The amount of other reaction components, namely the sterol or the amino acid in the product may be determined quantitatively in conventional manner, e.g. by thin-layer chromatography, or e.g. in the case of cholesterol as a sterol, by determining the iodine number of the product. Even without purification, less than 2% by weight, more generally less than 1.5% by weight, of these raction components is present. If the reaction component is an amino acid, its contribution to the acid number is thus low and generally can be neglected.

Determination of the molecular weight of the oligomer may be effected using conventional methods. Preferred methods are based on the lowering of vapour-pressure and gel permeation chromatography according to procedures well-known in the art, using polystyrene as standard. However, these methods may not give exactly the same results. For lower molecular weight ranges e.g. from 500 to 5,000, the values determined from the lowering of vapour-pressure are more reliable. For molecular weight ranges above 5,000 the values determined by gel permeation chromatography (Mw) are more reliable.

The products according to the invention preferably have an intrinsic viscosity of below $0.1 = (100 \text{ ml/g})$. This is conveniently measured in benzene or chloroform at 25.0° C. Such viscosity measurements may be effected in known manner.

The amino acid and sterol starting materials are either known or may be made in manner analogous to similar compounds. The hydroxycarboxylic acid oligomers may be made in conventional manner for producing oligomers containing the desired number of hydroxycarboxylic acid units.

The process may be effected by condensing lactic acid and/or glycolic acid in free form. When co-oligomers are being produced, appropriate quantities of glycolic acid and lactic acid are reacted together under dehydration conditions, e.g. heating to distil off water. The reaction times temperatures may be controlled within wide limits readily known to one skilled in the art, and as described in the examples.

Co-oligo-lactide-glycolides in free acid form having a molecular weight of from 500 to 5,000 and containing at least 50% by weight of lactic acid units, have been found to be exceptionally useful intermediates by virtue of the functional groups present, e.g. the free carboxyl group.

They are novel and form part of the present invention. Preferably they contain from 50 to 90%, especially 70% to 85% by weight of lactic acid units. Also preferably they have a molecular weight of from 500 to 3,000, more especially from 750 to 3,000 determined by lowering of vapour pressure, e.g. from 1,000 to 2,000.

The amide and ester products of the present invention are particularly useful in the production of pharmaceutical depot forms of pharmacologically active agents. Such depot forms may comprise a matrix of the amide or ester product containing the active agent. Preferred depot forms are implants (e.g. for subcutaneous administration) and microcapsules (e.g. for oral or parenteral administration, e.g. intramuscular administration).

The present invention accordingly provides a pharmaceutical depot form comprising a matrix of a product according to the invention containing a pharmacologically active agent, e.g. a polypeptide.

The depot forms are novel and form part of the invention.

The depot forms may be made in conventional manner, the amides and ester products of the invention being easy to handle, and often incorporating a high concentration of active agent. Moreover, the depot forms may exhibit particularly advantageous characteristics for releasing the active agent, e.g. in a more regular manner than known polylactic acids and co-polylactide-glycolides of high molecular weight and over a prolonged period. Moreover the amides and esters of the invention may be made into matrix forms which degrade into physiologically acceptable products which may disintegrate in the body fluids within a short time after all the active agent has been released, thereby allowing repeated administration without build-up of oligomers.

In order to produce microcapsules, the active agent my be dissolved in a volatile solvent such as chloroform. A solution of the amide or ester product of the invention e.g. in the same solvent, may then be added. The resultant homogeneous mixture may then be sprayed into air and during spraying dried to form an microcapsules.

Alternatively the active agent may be dissolved or suspended and the amide or ester product of the invention may be dissolved in a volatile, water immiscible solvent.

The organic phase may then be mixed vigorously with a stirred aqueous solution optionally containing gelatine or polyvinylpyrrolidone as an emulsifier. The organic solvent is removed from the resultant emulsion and the resultant microcapsules are filtered off or separated by centrifuging, washed e.g. in a buffer and dried.

In order to produce implants the active agent may be mixed with the amide or ester product of the invention and dissolved in a volatile solvent. The solvent may be evaporated and the residue group up. An extrusion may be formed in conventional manner, which is then cut up to produce implants.

Depending on the active ingredient, the microcapsules may take up an average of up to 60% by weight of the active ingredient. The implants are preferably prepared in such a manner that they contain up to 60% e.g. 1 to 20% by weight of the active agent. For the active ingredient salmon calcitonin, microcapsules may be prepared containing at most 3%, especially about 1.5% and implants containing up to 8% of the active agents.

The microcapsules may have a diameter from a few submicrons to a few millimeters. For pharmaceutical microcapsules, diameters of at most about 250 microns, e.g. 10 to 60 microns, are strived for, in order to facilitate passage through the injection needle.

The depot forms of the invention may be used to administer very different classes of active agents, e.g. biologically active compounds such as contraceptives, tranquilisers, steroids, sulphonamides, vaccines, vitamines antimigraine drugs, enzymes, bronchodilators, cardiovascular materials, analgesics, antibiotics, antigens, anti-convulsants, anti-inflammatory agents, anti-Parkinson drugs and anti-material drugs.

The depot forms of pharmaceutical compositions may be used for known indications of the relevant active agents.

The quantity of the active agent and of the depot forms to be administered is dependent on various factors, e.g. the conditions to be treated, the duration of treatment desired, the rate of release of the active agent and the biological degradability of the oligomer matrix.

The desired conditions can be formulated using techniques well known in the art. The amount of active agent required and the rate of release thereof may be determined using in vivo or in vitro techniques, e.g. measuring the concentration of active agent in the blood serum and for how long an acceptable level lasts. The degradability of the matrix can also be followed using in vivo or in vitro techniques, e.g. measuring the amount of lactic or glycolic acid or oligomers thereof in the blood or by histological techniques.

The deport forms of the invention may be administered e.g. subcutaneously or intramuscularly in the form of microcapsules, as a suspension in a suitable liquid carrier or subcutaneously in the form of implants.

Generally at least 40% by weight of the matrix desintegrates in the body fluids within 3 months.

Another administration of the depot form may be made when the matrix oligomer has disintegrated sufficiently, e.g. after 1 to 2 months.

Examples of dosages for preferred compounds include:

For bromocriptine for inhibition of prolactin secretion a depot form may be produced to release daily about 2.5 to 7.5 mg bromocriptine at over about 10 to 15 days, e.g. containing about 20 to 100 mg bromocriptine.

For salmon calcitonin for the treatment of Morbus Paget a depot form may be produced to release daily about 10 to 30 micrograms salmon calcitonin over about 10 to 15 days, e.g. containing about 100 to about 500 micrograms salmon calcitonin.

Depot forms for other active agents may be formulated in analogous manner.

A pharmaceutical depot e.g. microcapsule and implant forms comprising a biodegradable polymer matrix and salmon calcitonin as pharmaceutically active agent are novel and form part of the invention. Spray dried microcapsules of a biodegradable polymer matrix containing bromocriptine mesylate as pharmaceutically active agent are also novel and form part of the invention.

These salmon calcitonin forms and bromocriptine forms may be made not only from the amides and ester products mentioned herin but also other oligomers and polymers. They may be made and administered in known manner or as disclosed herein in respect of depot forms produced from amide and ester products of the invention.

In the following Examples all temperatures are in degrees Centigrade and are uncorrected. Di-lactide refers to the cyclic lactone.

CHEMICAL PREPARATION OF STARTING MATERIALS

A.1 D,L-oligo-lactic acid 1600 g of optically inactive lactic acid are placed in a 2 l flask equipped with a thermometer, gas input capillary, Liebig condenser and vacuum facilities, and then heated in an argon atmosphere to a bath temperature of 160°. A clear colourless distillate is produced after 8 hours. Distillation continues for 4 hours at 100 torr, then for a further 4 hours at 20 torr, and then for 3 hours at 10 torr. Acid number of the slurry: 30, corresponding to an average molecular weight of 1870. The hot product is transferred onto a porcelain dish, allowed to cool and then pulverised.

Melting range: 40°–60°, acid number: 30.

Molecular weight (determined by lowering of vapour-pressure): 2000. The product is completely amorphous and dissolves readily in acetone and methylene chloride at room temperature.

D,L-oligo-lactic acid and L-oligo-lactic acid products having the following data are produced in analogous manner, products of higher molecular weights requiring longer and products of lower molecular weights shorter reaction times:

|   |   | intrinsic viscosity | acid number | molecular weight on basis of acid number | molecular weight on basis of lowering of vapour-pres. |
|---|---|---|---|---|---|
| A.2 | D,L-oligo-lactic acid | 0.04 | 25.0 | 2240 | 2400 |
| A.3 | D,L-oligo- | 0.03 | 25.0 | 2240 | 2100 |

-continued

| | intrinsic viscosity | acid number | molecular weight on basis of acid number | molecular weight on basis of lowering of vapour-pres. |
|---|---|---|---|---|
| A.4 | lactic acid L-oligo-lactic acid | | 104 | 538 |
| A.5 | L-oligo-lactic acid | | 63.5 | 882 |
| A.6 | L-oligo-lactic acid | | 48.5 | 1154 |
| A.7 | D,L-oligo-lactic acid | 0.01 | 27.0 | 2070 |
| A.8 | D,L-oligo-lactic acid | 0.01 | 18.8 | 2980 |
| A.9 | D,L-oligo-lactic acid | 0.03 | 23 | 2400 |
| A.10 | D,L-oligo-lactic acid | | 12 | 4590 |

A.11 Co-oligo-D,L-lactide-glycolide 1350.0 g of optically inactive lactic acid (72% by weight aqueous solution) and 150.6 g of glycolic acid are placed in a 2 l flask equipped with a thermometer, gas input, reflux condenser and vacuum facilities.

A weak current of argon is passed through the mixture, which is heated to a slurry temperature of 160°. The reflux condenser is replaced by a descending cooler adapted to remove distillate. After 8 hours 295 ml of distillate containing water are separated. The pressure is then reduced to and kept at 100 torr for 2 hours. The pressure is further reduced and kept at 20 torr for 8 hours. The slurry temperature is raised to 180°. The acid number of the slurry determined at this point is 48, corresponding to an average molecular weight of 1170. The pressure is then kept at 10 torr for a further 8 hours. The acid number is then 31.7 (molecular weight 1770). In total 555 ml of distillate are collected. The hot product is transferred onto a porcelain dish, allowed to cool an then pulverised. A light yellow powder is obtained, melting range: 40°–60°. Acid number is 31.7 Molecular weight, determined by lowering of vapour pressure: 1900, Micro-analysis: C 48.20%, H 5.61%, O 46.30%. 84 weight percent lactic acid units by NMR.

Co-oligo-D,L-lactide-glycolide products having the following data are produced in analogous manner:

| | acid number | molecular weight on basis of acid number | molecular weight on basis of lowering of vapour pressure | % by weight lactic acid from NMR | micro analysis % by weight | |
|---|---|---|---|---|---|---|
| A.12 | 23 | 2430 | 1820 | 89 | | |
| A.13 | 23 | 2430 | 1870 | 81 | | |
| A.14 | 29 | 1930 | 1770 | 84 | 48.2 5.6 | 46.3 |
| A.15 | 31 | 1800 | 1800 | 75 | 48.0 5.5 | 46.7 |
| A.16 | 28 | 2000 | 1910 | 71 | | |
| A.17 | 25 | 2240 | 1820 | 50 | | |

A.18 Oligo-glycolic acid 500 g of solid glycolic acid are placed in a 750 ml flask equipped with a thermometer, Liebig condenser and gas input capillary, and heated to a slurry temperature of 160° C. Distillation is effected firstly for 2 hours at normal pressure, then for 2 hours at 100 torr, and finally for a further two hours at 10 torr. The slurry, which is still hot, is transferred onto a porcelain dish, and solidifies immediately to a white, waxy mass.

Acid number: 79: molecular weight: 750 (determined by lowering of vapour pressure), melting range: 140°–190° C.

CHEMICAL PREPARATION OF THE AMIDES AND ESTERS ACCORDING TO THE INVENTION

B.1 (Co)oligo-D,L-lactide-glycolide-cholesterylester 927 g of the co-oligo-D,L-lactide-glycolide of Example A.15 and 298.2 g of cholesterol (0.77 mol; molar ratio of co-oligomer to cholesterol=1:1.5) are melted while stirring in a 2 l flask equipped with a thermometer, Liebig condenser, gas input and stirrer and containing an argon atmosphere. The temperature of the slurry is 170°. Stirring is effected for 6 hours at 10 torr. The hot yellow-brown mass is then transferred onto a porcelain dish and allowed to cool.

Acid number 14.6, Saponification value: 588; iodine value: 14.0: Molecular weight determined by lowering of vapour-pressure: 1140. Free cholesterol content: 1.0–2.0% by weight determined by thin-layer chromatography; Free di-lactide: 1.0% by weight; Water content: 0.25%. Melting range: 70°–90°. Microanalysis: C 56.60%, H 6.90%, O 36.30%.

D,L-oligo-lactic acid cholesteryl ester (Examples B2 and B3) and Co-oligo-D,L-lactide-glycolide cholesteryl ester (Example B4) products having the following data are produced in an analogous manner:

| Product | B.2 | B.3 | B.4 |
|---|---|---|---|
| Molar ratio of oligomer: cholesterol | 1:1 | 1:2 | 1:1.5 |
| Acid number | 17.6 | 13.2 | 15.7 |
| Saponification value | 643 | 582 | 575 |
| Molecular weight by lowering vapour-pressure | 1370 | 1150 | 1140 |
| Content of di-lactide (% by weight) | 1.3 | 0.99 | 1.0 |
| Content of free cholesterol (% by weight) | 0.7–1.0 | 1.0–1.5 | ca. 1.0 |
| Water content (% by weight) | | | 0.20 |
| Melting range (TLC) | 40–50° | 40–50 | 60–80° |
| C (% by weight) | 54.0 | 57.6 | 56.9 |
| H (% by weight) | 6.4 | 6.8 | 6.8 |
| O (% by weight) | 39.2 | 35.8 | 36.3 |
| % by weight cholesterol in mixture employed | 13.1 | 23.2 | 24.1 |
| Prepared from oligomeric hydroxycarboxylic acid of Example | A.9 | A.9 | A.11 |

B.5 D,L-oligo-lactoyl-N-(L)-phenylalanine (a) Amide of DL-oligo-lactic acid and hydroxysuccinimide 30 g (0.015 ml) of D,L-oligo-lactic acid from Example A.7 and 1.7 g (0.015 mol) of N-hydroxysuccinimide are suspended in 100 ml of ethyl acetate. 3.1 g (0.015 mol) of dicyclohexylcarbodiimide are added portionwise in 1 minute to this suspension. The addition is exothermic. The mixture is cooled in water bath. The brown-beige suspension changes slowly to a very thick white suspension. After 23 hours, the suspension is filtered off and the filter cake is washed twice with 10 ml of ethyl acetate. The clear mother liquor is evaporated in a rotary evaporator at a bath temperature of 50° C. The very viscous mass is dried 24 hours at 50° in vacuum. A slightly yellow resinous product is obtained having the following NMR spectrum:

1H—NMR 360 MHz, solvent CDCl$_3$: ppm 5.50 (m, 1H, CH—OH at end of polymer chain); 5.18 (m, 27H, CH—C— in the polymer chain); 4.39 (m, 1H, CH—C—O— at end of polymer chain); 2.86 (S, 4H, CH$_2$ in succinimidyl); 1.72 (m, 3H, CH$_3$—C—OH at end of polymer chain; 1.57 (m, 81H, CH$_3$— in the chain); 1.48 (d, 3H, CH$_3$—C— at end of polymer chain).

(b) D,L-oligo-lactoyl-N-(L)-phenylalanine 2.4 g (0.0145 mol) of L-phenylalanine are suspended in a solution of 1.2 g (0.0145 mol) of sodium bicarbonate in 104 ml of water. After stirring for 10 minutes, a solution of 30.0 g (0.0145 mol) of (±)oligo-lactoylhydroxysuccinimide in 104 ml of tetrahydrofuran is added dropwise within 25 minutes. The addition is slightly exothermic. The reaction mixture is stirred for 72 hours at room temperature. Finally the pH is 6.6 and is adjusted to 4.0 using 1N hydrochloric acid. The phases are separated and the aqueous phase is extracted twice with 200 ml of methylene chloride. The combined organic phases are washed twice with 100 ml of water. The resultant solution is dried over magnesium sulphate and evaporated in a rotary evaporator. The residue is dried over 48 hours at room temperature in vacuum. A slightly yellow substance is obtained.

NMR-360 MHz in CDCl$_3$: ppm 7.25 (m, 3.8H, Ar—NH); 5.38 (8m, 1H, —CH—C— at end of polymer chain); 5.21 (m, 27H, —CH—C— in the polymer chain); 5.06 (m, 0.6H, CH—OH at end of polymer chain); 4.38 (m, 0.6H, —CH—N); 3.07–3.32 (m, 1.2H, CH$_2$-Ar); 1.57 (m, 81H, CH$_3$ in the polymer chain); 1.46 (m, 6H, CH$_3$— at end of polymer).

GPC: $M_w$ 4860; $M_n$ 3200; $M_w/M_n$ = 1.52; acid number 17.3.

According to NMR and Gel permeation chromatography results the product is pure.

Purification of amides and esters of the invention

C.1 1000 g of the co-oligo-D,L-lactide-glycolide-cholesteryl ester from Example B.4 are dissolved in 2.5 l of isopropyl acetate at room temperature. The solution is put onto a chromatography column filled with silicagel [Merck 60 grain size 0.063–0.200 mm (No. 7734)], and is eluted with isopropyl acetate. The individual fractions are evaporated until dry in a rotary evaporator at a bath temperature of 140°, and then dried for another 6 hours at 130° and at 1 torr. The following Table gives data on the individual fractions:

| Fraction No. | Dry weight in g | Acid number |
| --- | --- | --- |
| 1 | 1.8 | 0.2 |
| 2 | 22.9 | 0.4 |
| 3 | 98.0 | 0.2 |
| 4 | 192.0 | 0.6 |
| 5 | 196.0 | 3.8 |
| 6 | 136.9 | 8.0 |
| 7 | 81.8 | 12.8 |
| 8 | 65.8 | 15.5 |
| 9 | 51.3 | 20.3 |
| 10 | 22.2 | 24.9 |
|  | 868.9 |  |

The first 4 fractions are combined, dried, mixed, heated for 2 hours at 130° and pulverised after cooling. Free cholesterol: 0.5%. Acid number: 0.5 Iodine value: 13.7, Saonification value: 600, Heavy metal content below 20 ppm, Molecular weight (determined by lowering of vapour-pressure): 1320, melting range: 40°–60°, dilactide content below 0.2% by weight, diglycolide content below 0.5% by weight, Isopropyl acetate content: 0.02%, ignition residue: below 0.03%, Microanalysis: C 59.70, H 7.62, O 32.90, Molecular mass (GPC**): $M_w$ = 2980 $M_n$ = 2000.

C.2 The co-oligo-D,L-lactide-glycolide-cholesteryl ester from Example B.1 is purified in analogous manner. The fractions having an acid number of less than 1.5 are combined and further processed. A product is obtained having the following specifications:

Free cholesterol content: 1.5%, Acid number: 1.2, Iodine value: 13.7, Saonification value: 590, Heavy metal content below 20 ppm, molecular weight (determined by lowering of vapour-pressure) 1160, Melting range: 40°–60°, Free lactide* content 0.2% by weight, Free glycolide* content below 0.5% by weight, Isopropyl acetate content 0.02%, Ash content 0.03% by weight, Microanalysis: C 59.50, H 7.60, O 33,20, molecular mass(GPC**): $M_w$ = 2850, $M_n$ = 2021.

*cyclic component
**GPC = gel permeation chromatography

Micro-encapsulation of active agents

D.1 A solution of 9850 mg of D,L-oligo-lactoyl-N-(L)-phenylalanine (from Example B.5) in 180 ml of methylene chloride is added to a solution of 150 mg of salmon calcitonin in 20 ml of methanol. The resultant homogenous phase is sprayed dried into microcapsules (Apparatus: Mini-Spray Dryer, (Büchi, Type 190)) which is previously adjusted to constant conditions with a solvent mixture consisting of 10% methanol and 90% methylene chloride; the temperature at the input is regulated to 60±1° and at the output to 39±1°. The pump capacity is set at about 600 ml/hour. Ventilation is regulated to position 14–15 and the current of air is set at 300–350 1N/hour. The heating resistance is 3.2.

The microcapsule matrices obtained in this way contain 91% of the theoretical salmon calcitonin content. The microcapsules can be easily dispersed and applied i.m. by an injection needle.

In analogous manner microcapsules using the polymer produced from Example A.17 (a free acid polymer) were produced for comparison.

The in vitro release was measured at pH 4.2 and 37° (acetate buffer).

| Results: | % Release of salmon calcitonin | |
| --- | --- | --- |
| Time min. | Matrix from B.5 | Matrix from A.17 |
| 5 | 1.5 | 16.2 |
| 30 | 5.6 | 41.6 |
| 60 | 8.1 | 46.0 |
| 120 | 10.0 | 51.4 |
| 240 | 10.1 | 52.3 |
| 360 | 10.2 | 52.8 |
| 1320 | 9.4 | 52.0 |

D.2 300 mg of salmon calcitonin are dissolved in 40 ml of methanol and 9.70 g of D,L-oligolactic acid cholesteryl ester (B.3) are dissolved in 360 ml of methylene chloride. The two solutions are mixed together and the procedure described unter D.1 is repeated.

After i.m. injection into rabbits of microcapsules of the types D.1 and D.2 in a quantity which contains 2000 IE of the peptide (100 IE = 25 ug), calcitonin concentrations of ca. 0.5–1 ng/ml plasma were measured during 1 week using a specific radio-immunoassay.

D.3 2.5 g of bromocriptine mesylate are dissolved in 20 ml of methanol and 7.5 g of D,L-oligolactoyl-N-(L)-phenylalanine (Example B.5) are dissolved in 180 ml methylene chloride, the two solutions are mixed together and spray-dried in analogous manner to that disclosed in Example D.1 under the following conditions:

Ouput capacity of the pump: 600 ml/h.
Temperature at input: 59°.
Temperature at output: 39°.
Ventilation at position 11.
Current of air at 310 Nl/h.

The microcapsules obtained have a diameter of less than 0.125 mm and are very easily dispersable and applicable by an injection needle, without forming aggregates. The microcapsules contain 20% of bromocriptine mesylate, calculated on the total weight.

The in vitro release at pH 4.0 and 37° (citrate/phosphate buffer) is measured at 120 rpm by the rotating paddle method (USP XX, page 959).

| Results Time (min.) | % release of bromocriptine mesylate matrix of B.5 |
|---|---|
| 60 | 2.4 |
| 120 | 2.4 |
| 180 | 2.5 |
| 300 | 2.6 |
| 420 | 2.6 |
| 1440 | 3.1 |

E.4 10 g of purified D,L-co-oligo-lactide-glycolide-cholesteryl ester from Example C.2 are dissolved, while stirring, in 250 g methylene chloride. 10 g of dihydroergotamine are added and mixed vigourously. The obtained suspension is sprayed within 10 minutes in a spray drier at 55° C. The formed microcapsules are obtained as a free-flowing powder. The particle size of the microcapsules is below 0.125 mm. In a comparison test, a quantity of the pure active ingredient and a similar quantity of the active ingredient incorporated into microcapsules are each dissolved in the same volume of buffer solution (pH=4) at 37° C. During the time taken for the pure active ingredient to dissolve by almost 100%, under the same conditions only 7% of the active ingredient was released from the capsules, which indicates that at least 93% of the active ingredient is absorbed and retained in the capsules.

Implant preparation

F.1 25 mg of salmon calcitonin and 475 mg of D,L-co-oligo-lactide-glycolide-cholesteryl ester (see Example B.1) are mixed and pulverised. The resultant powder is dissolved in 25 ml of methylene chloride.

The solvent is evaporated within 20 minutes at room temperature in a rotary evaporator under reduced pressure. The residue is warmed to 50° for 10 minutes in a water bath. The film obtained is pulverised and extruded with a diameter of 1 mm at a temperature of 66°–68°. The obtained form is used as an implant when cut into lengths of 20 mm. This implant is injected subcutaneously.

Implants of the following components are prepared in a similar manner:

F.2 25 mg of ketotifen and 475 mg of D,L-co-oligo-lactide-glycolide-cholesterylester (see Example B.4)

F.3 25 mg of bromocriptine mesylate and 475 mg of D,L-oligo-lactide-cholesterylester (see Example B.2)

F.4 25 mg of dihydroergotamine and 475 mg of D,L-co-oligo-lactide-glycolide-cholesterylester (see Example C.1).

Rate of decomposition in an aqueous medium (a) In vitro Test

It is found that amide and ester products according to the invention decompose in water more rapidly than polymeric hydroxycarboxylic acids and (co) polymeric hydroxycarboxylic acids. Additionally, they decompose slower than the free co-oligomeric hydroxycarboxylic acids:

Films of the following products are stored in water at 37°, and their weight losses are evaluated after a period of time.

| | Weight loss after | | | |
|---|---|---|---|---|
| | 13 | 40 | 54 | 90 days |
| Co-oligo-D,L-lactide-glycolide (see Example A.15) | 37% | | 100% | |
| Copoly-D,L-lactide-glycolide 75% by weight lactide; $M_w = 28,000$ | | 0.1% | | |
| Co-oligo-D,L-lactide-glycolide cholesterylester (Example C.2) | 2% | | | 45% |
| L-polylactic acid $M_w = 40,000$ intrinsic viscosity = 0.68 | | | | 2% |

(b) In vivo Test

Small discs of 7 mm diameter and 0,5 mm thickness of the polymer C.2 under (a) were implanted intraperitoneally in rats.

The degradation of the oligomer product under C.2 was 39% (determined by weight of the removed discs).

What we claim is:

1. A modified oligomer consisting of units of lactic acid and/or glycolic acid, the oligomer moiety having a molecular weight of from 500 to 10,000, in which the terminal carboxy group is in the form of an amide of an alpha amino acid.

2. The modified oligomer of claim 1 wherein the terminal carboxy group is in the form of an alpha amino acid amide.

3. The modified oligomer of claim 1 wherein the terminal carboxy group is in the form of phenylalanine.

4. The modified oligomer of claim 1 wherein the oligomer moiety contains lactic acid units.

5. The modified oligomer of claim 1 having a molecular weight of from 750 to 5,000.

* * * * *